United States Patent
Morman et al.

(10) Patent No.: US 6,761,709 B2
(45) Date of Patent: Jul. 13, 2004

(54) LIQUID RECEPTION MEDIUM WITH LIQUID ACTIVATED MECHANICAL MASS TRANSPORT MEANS

(75) Inventors: Michael Tod Morman, Alpharetta, GA (US); Bryan David Haynes, Cumming, GA (US); Thomas Harold Roessler, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/121,353

(22) Filed: Apr. 12, 2002

(65) Prior Publication Data

US 2002/0128616 A1 Sep. 12, 2002

Related U.S. Application Data

(62) Division of application No. 09/353,470, filed on Jul. 13, 1999, now Pat. No. 6,423,883.

(51) Int. Cl.[7] .................................................. A61F 13/15
(52) U.S. Cl. ........................... 604/385.101; 604/385.12
(58) Field of Search ................................. 604/361, 364, 604/378, 385.101, 385.12

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,683,914 A | 8/1972 | Crowley | 128/285 |
| 3,692,618 A | 9/1972 | Dorschner et al. | 161/72 |
| 3,802,817 A | 4/1974 | Matsuki et al. | 425/66 |
| 3,841,333 A | 10/1974 | Zalucki | 128/285 |
| 3,867,924 A | 2/1975 | Bucalo | 128/285 |
| 3,881,491 A | 5/1975 | Whyte | 128/287 |
| RE28,674 E | 1/1976 | Guyette | 128/285 |
| RE29,061 E | 12/1976 | Bucalo | 128/285 |
| 4,340,058 A * | 7/1982 | Pierce et al. | 128/287 |
| 4,340,563 A | 7/1982 | Appel et al. | 264/518 |
| 4,486,191 A | 12/1984 | Jacob | 604/330 |
| 4,533,352 A * | 8/1985 | Van Beek et al. | 604/317 |
| 4,663,220 A | 5/1987 | Wisneski et al. | 428/221 |
| 4,704,116 A | 11/1987 | Enloe | 604/385 A |
| 4,790,836 A * | 12/1988 | Brecher | 604/359 |
| 5,304,599 A | 4/1994 | Himes | 525/98 |
| 5,327,897 A | 7/1994 | Andresen | 128/762 |
| 5,330,459 A | 7/1994 | Lavon et al. | 604/385.1 |
| 5,332,613 A | 7/1994 | Taylor et al. | 428/152 |
| H1585 H * | 8/1996 | Ahr | 604/378 |
| 5,643,241 A | 7/1997 | Ahr et al. | 604/385.1 |
| 5,678,564 A * | 10/1997 | Lawrence et al. | 600/574 |
| 5,681,297 A | 10/1997 | Hashimoto et al. | 604/355 |
| 5,769,834 A | 6/1998 | Reiter et al. | 604/385.1 |
| 5,865,825 A | 2/1999 | Schlinz | 604/385.2 |
| 5,902,297 A | 5/1999 | Sauer | 604/385.1 |
| 5,911,222 A | 6/1999 | Lawrence et al. | 128/761 |
| 6,007,524 A | 12/1999 | Schneider | 604/327 |
| 6,071,267 A * | 6/2000 | Zamierowski | 604/289 |
| 6,235,009 B1 * | 5/2001 | Skow | 604/317 |
| 6,262,331 B1 * | 7/2001 | Nakahata et al. | 604/383 |
| 6,432,097 B1 * | 8/2002 | Ahr et al. | 604/385.19 |
| 6,450,995 B1 * | 9/2002 | Prabhakar | 604/317 |

* cited by examiner

*Primary Examiner*—John J. Calvert
*Assistant Examiner*—Catharine L. Anderson
(74) *Attorney, Agent, or Firm*—William D. Herrick

(57) ABSTRACT

A liquid reception device is disclosed as a component, for example, of a personal care product such as a disposable diaper, an incontinent garment, or for other applications such as, for example, an industrial soaker pad or the like. The device includes liquid activated means to move a liquid insult from a target zone to a peripheral zone. The liquid activated transport means is operated mechanically by suction created by compression or vacuum or by physical movement of a liquid container from the target zone to the peripheral zone. The disclosed device provides increased use of available liquid handling capacity.

9 Claims, 7 Drawing Sheets

LIQUID RECEPTION MEDIUM WITH LIQUID ACTIVATED MECHANICAL MASS TRANSPORT MEANS

This application is a divisional of application Ser. No. 09/353,470 entitled Liquid Reception Medium with Liquid Activated Mechanical Mass Transport Means and filed in the U.S. Patent and Trademark Office on Jul. 13, 1999, now U.S. Pat. No. 6,423,883. The entirety of application Ser. No. 09/353,470 is hereby incorporated by reference.

FIELD OF THE INVENTION

The present invention relates to media for reception of liquid such as absorption, retention, and transfer components of personal care products like disposable diapers, training pants, swimwear, incontinent protective devices and feminine care sanitary napkins and the like. While many improvements have been made to liquid reception media for these and other uses, some products still tend to be bulky and, in use, cause the wearer to be self conscious. Moreover, packaging, shipping and storage of such bulky products represent significant costs. Finally, disposal of used product has been indicated by some to represent an opportunity for environmental improvement. It has been long recognized that a more efficient medium for receiving, transfer and/or absorption would permit significant reduction in the amount of absorbent material needed and favorably impact each of the above issues. The present invention is directed to such a liquid reception medium.

BACKGROUND

One measure of the efficiency of a liquid absorbent medium is its ability to move the liquid being absorbed within the medium from the point of delivery to areas throughout the entire absorbent medium so that the total available capacity of the medium to absorb is utilized. Much research effort has been expended developing ways to accomplish this movement of liquid. For example, special fiber shapes and spacing have been used to create and enhance the capillary forces which cause fluids to move in an absorbing medium, and treatments have been developed that act on liquids being absorbed and the absorbing medium itself. In addition, the configuration of the medium has been modified such as by creating embossed channels or folds intended to direct liquid movement. While these efforts have had a measured degree of success, there remains a need for even better measures to quickly move relatively large liquid volumes (insults) from a delivery or target zone to a peripheral area either within the liquid receiving component or in another absorbent component. The result will reduce leakage and/or allow reduced amounts of absorbent material to be used to make more conforming products and provide environmental benefits.

Capillary movement of liquids either using the capillary structure between fibers or pore structures within foams, for example, is relatively slow. Movement of mass quantities of liquid resulting from gush or surge insults can, of course, be accomplished by collecting the liquid and displacing it by physical means to another area of the absorbent product. Practical means for accomplishing this displacement, however, are not well defined or developed to date. One effort described in U.S. Pat. No. 5,769,834 to Reiter et al., relies on an apertured tube and pumping action from decompression and compression by bodily movements of a wearer of a diaper, as an example. The liquid movement is thus dependent on the movement of the wearer. U.S. Pat. No. 5,902,297 to Sauer is directed to an absorbent article with conduit means for collecting and transporting fecal matter. The present invention relates to different mechanical structures of absorbent product components to accomplish the desired result in a reliable and effective manner.

SUMMARY OF THE INVENTION

The present invention provides a liquid reception device having one or more component layers and that includes a layer having a target zone and that includes in the device a peripheral absorption zone either within or outside the layer having a target zone. A liquid transport means is included within the target zone and extends to the peripheral zone. Upon liquid contact the liquid transport means is activated to move a mass amount of liquid from the target zone to a peripheral zone. The liquid transport means can be, for example, a tube which is connected to a suction device and is sealed by a liquid dissolvable seal. When contacted by liquid, the seal is dissolved and the end of the tube or other previously sealed part opened to draw liquid by means of the suction device. Another means can be a collapsed sealed tube containing a liquid expandable material such as a superabsorbent or collapsed foam. When the seal is dissolved, the collapsed tube is forced to expand. The expansion creates a void volume and thus a vacuum. The liquid is pulled into the tube by the vacuum. As the liquid contacts the superabsorbent, the superabsorbent swells, causing the tube to further expand. Ideally, the tube will readily expand to a larger dimension that its original, pre-compressed dimension so the absorption/expansion/vacuum generation cycle will continue. Another transport means includes a collection device attached by a dissolvable adhesive in the target zone and also by elastic means to an area in the peripheral zone. Liquid contact causes the collection means to be released from the target zone and displaced to the peripheral zone. The collection device could be a stretched superabsorbent fiber which is permanently attached in the periphery of the product and attached in the target area by a slowly dissolving water soluble adhesive. The filament would absorb liquid, the adhesive dissolve, and be pulled up into the periphery of the product. In all cases the structure requires only liquid contact to activate the mechanical liquid transport means.

DETAILED DESCRIPTION OF THE INVENTION

Definitions

Figure 1:
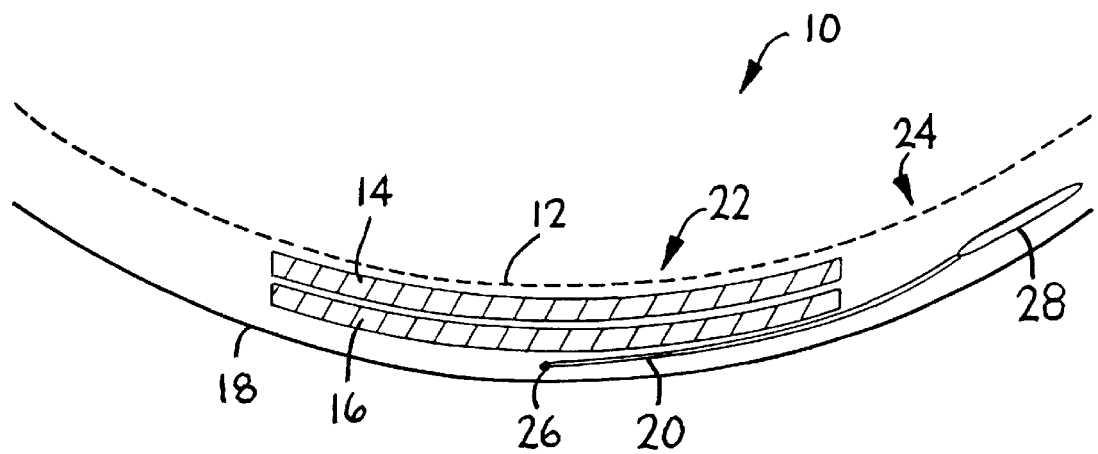
FIG. 1 is a partial view in cross-section of an absorbent product incorporating one embodiment of the present invention.

As used herein, the term "tube" means an element having a length exceeding its width and a central portion along its length that permits liquid flow and that is surrounded by an outside skin or portion that contains liquid within the central portion. An obvious example is a drinking straw, but other examples can include solid elements with a high liquid transport center containing superabsorbent fibers.

As used herein, the term "medium" means a structure having interconnected pores that allow liquid to enter and flow in one or more directions. Examples include foams and fibrous webs.

As used herein, the term "superabsorbent" means a water-swellable, water-insoluble organic or inorganic material capable, under the most favorable conditions, of absorbing at least about 10 times its weight and, preferably, at least about 20 times, more preferably about 30 times, its weight in an aqueous solution containing 0.9 weight percent of sodium chloride. Organic materials suitable for use as a superabsorbent material of the present invention can include natural materials such as agar, pectin, guar gum, and the like, as well as synthetic materials such as synthetic hydrogel polymers. Such hydrogel polymers include, for example, alkali metal salts of polyacrylic acids, polyacrylamides, polyvinyl alcohol, ethylene maleic anhydride co-polymers, polyvinyl ethers, hydroxypropyl cellulose, polyvinyl morpholinone, and polymers and copolymers of vinyl sulfonic acid, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Cross-linking may, for example, be by irradiation, or by covalent, ionic, Van der Waals, or hydrogen bonding. Preferred superabsorbent materials are shell cross-linked so that the outer surface or shell of the superabsorbent particle, fiber, flake, sphere, etc. possesses a higher cross-link density than the inner portion of the superabsorbent. The superabsorbent materials may be in any form suitable for use in absorbent composites including particles, fibers, flakes, spheres, and the like. In one preferred embodiment of the present invention, the superabsorbent material comprises particles of hydro-colloids, preferably anionic hydro-colloids.

As used herein, the term "liquid" has its usual meaning and includes nonparticulate materials capable of flowing and assuming the shape of an opening or container receiving them. Examples include aqueous liquids such as urine and blood products for which personal care products are designed and do not exclude particulate components that do not prevent the described flow such as may be found in runny bowel movements ("BM") for example.

As used herein, the term "mechanical" means an operation that includes movement of a structure or element of a structure. Examples include 1) expansion or contraction of walls of a space defining component such as a tube or bulb or 2) stretching or contraction of an elastic component.

As used herein, the term "target" means an area, zone, or volume expected to be one of the first to receive a liquid insult for a particular product application. It will be recognized by those skilled in the art that the target area size will vary depending on the particular product applications and wearer. However, in general, the target area will include that portion of the medium which the liquid involved would occupy or flow after a three second period in use. For purposes of this description, the target may be covered by another layer or component, such as a diaper liner, for example, and in that context may not be the first liquid contact point.

As used herein, the term "peripheral" means an area outside of the target area.

As used herein, the term "mass transport" means movement of the liquid involved at a rate that is at least effective to maintain the ability of the target zone to receive a second or additional insult without exceeding its absorbent capacity as indicated by excessive leaking.

As used herein, the term "elastic" means an element having a retractive force from an elongation. Examples include a stretched rubber band.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "spunbonded fibers" refers to small diameter fibers which are formed by extruding molten thermoplastic material as filaments from a plurality of fine, usually circular capillaries of a spinnerette with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Levy, and U.S. Pat. No. 3,542,615 to Dobo et al. Spunbond fibers are generally not tacky when they are deposited onto a collecting surface. Spunbond fibers are generally not tacky when they are deposited onto a collecting surface. Spunbond fibers are generally continuous and have diameters larger than 7 microns, more particularly, between about 10 and 20 microns.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic, syndiotactic and random symmetries.

As used herein and in the claims, the term "comprising" is open and does not exclude additional elements, ingredients, or process steps which do not prevent operation of the invention.

EXAMPLES

For purposes of exemplifying the present invention, the particular product application is not critical. The invention will be described generally as a disposable diaper having basic components of a liner, absorbent layer, and backing and which may include additional components such as a surge layer. It will be apparent to those skilled in the art that the particular product may take numerous forms and include more or less elements. For example, a soaker pad may not require a liner, and an incontinent garment may have a belt, straps, or other ways to maintain its position on the wearer. These and other applications which can take advantage of the ability to rapidly mass transport in accordance with the invention are all contemplated and embraced by the description and claims which follow.

Turning to the drawings, FIG. 1 illustrates in cross-section a partial view of a disposable diaper 10 having a liquid permeable liner 12, absorbent layer 16, surge layer 14 and liquid impermeable backing 18. In this case the mass transport means is a tube 20 located between the absorbent layers 16 and the backing 18 and extending from the target area 22 to the peripheral area 24. The tube 20 is in communication with a collapsed expandable bulb 28 the peripheral area 24 and sealed by means of a liquid soluble seal 26 at the opposite end located in the target area 22. Upon liquid insult in the target area 22, contact between the liquid and seal 26 causes the seal to fail allowing the bulb 28 to expand drawing liquid through the tube 20 from the target area 22 to the peripheral area 24. If additional expansion is desired, the collapsed bulb may contain a superabsorbent that will expand when wetted and further expand the bulb drawing additional liquid through the tube.

Figure 2:
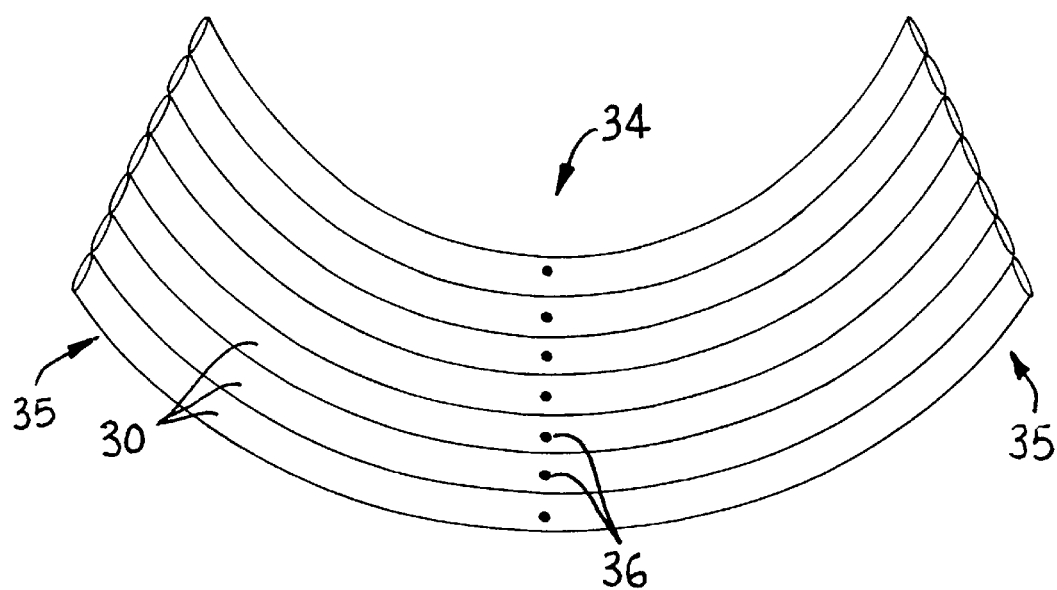
FIG. 2 is an enlarged view of a product like that of FIG. 1 using a different embodiment of the present invention.

FIG. 2 illustrates in schematic cross-section an alternative mechanism for moving liquid that includes a series of collapsed expandable tubes 30 next to each other and extending in the target area 34 to peripheral areas 35. Tubes 30 extend in both directions from target area 34 to peripheral areas 35, and each has a liquid soluble seal 36 in the target area 34. On liquid contact, the seal 36 dissolves allowing liquid to contact the expanding tubes which draws fluid into the tubes. The seals can be of differing thicknesses, compositions, etc. so the seals dissolve at different rates. Thus, first one seal dissolves and the associated tube expands and fills with liquid. A second seal dissolves and that tube fills and so on until the liquid is absorbed. When all the liquid is absorbed, untriggered tubes remain for the next insult. The arrangement of the tubes allows time delayed mass liquid transport as each tube becomes contacted with liquid. By controlling the amount and/or nature of the material sealing the tubes, provision may be made to accommodate a number of liquid insults over an extended time period. Such a structure finds particular application as, for example, an overnight bedpad.

Figure 3:
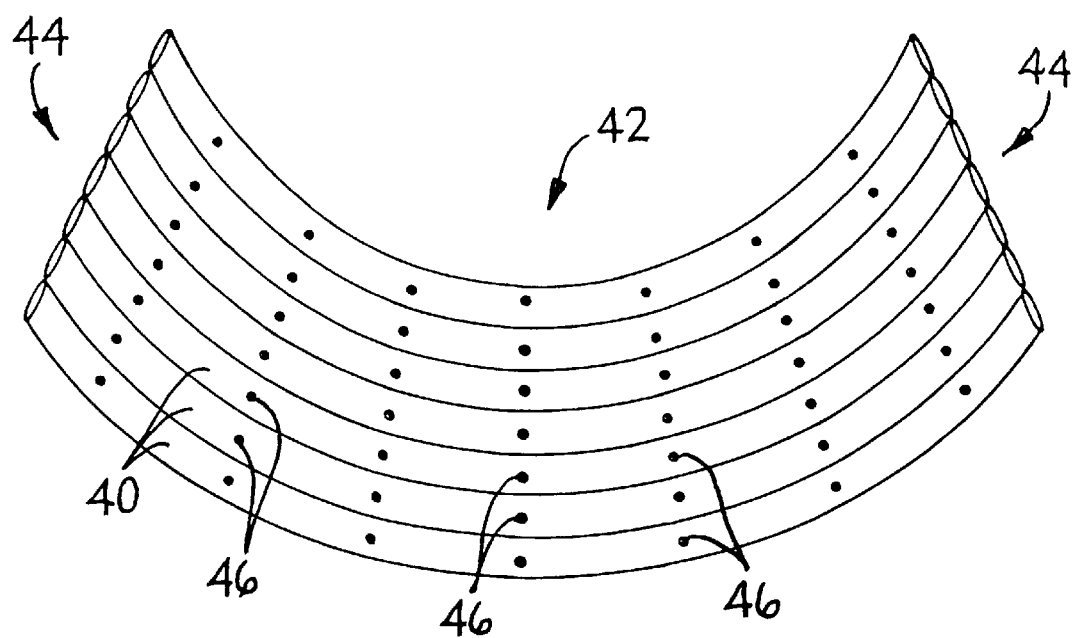
FIG. 3 is a view like that of FIG. 2 showing a further embodiment of the present invention.

FIG. 3 is a view of an embodiment like that of FIG. 2 except that in this case tubes 40 each have multiple liquid soluble seals 46 along its length which can extend outside of the target zone 42 into the peripheral zone 44. This arrangement accommodates multiple insults over a larger area of the product. It also provides additional paths the fluid can take in case the primary path is blocked by the swelling of a superabsorbent, e.g., gel blocking. By varying the amount of expandable material in the tubes the drawing forces on the liquid can be controlled to insure that the full capacity of each tube is available.

Figure 4:
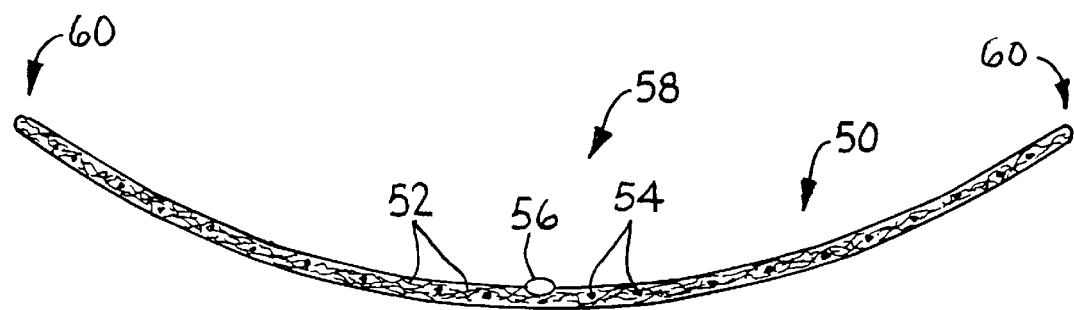
FIG. 4 is a view in cross-section of one liquid movement element in accordance with the present invention prior to liquid contact.
Figure 5:
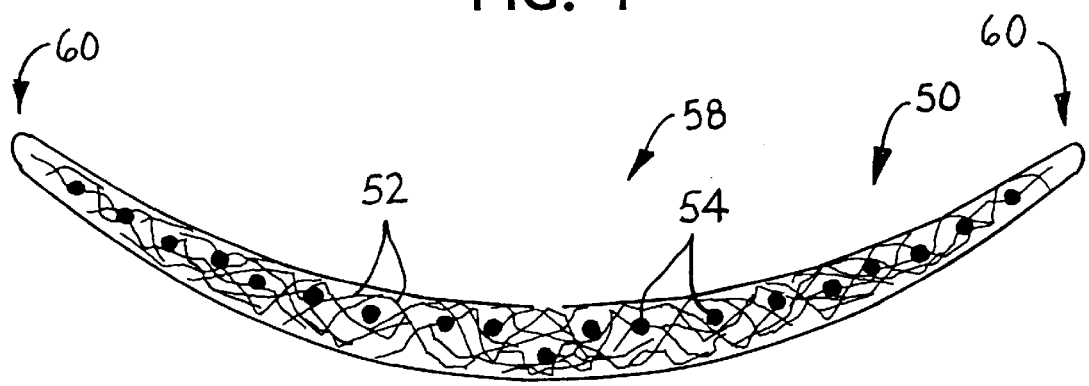
FIG. 5 is a view of the element of FIG. 4 after liquid contact.

FIGS. 4 and 5 illustrate in greater detail the operation of a tube 50 as described with respect to FIGS. 2 and 3. In this case tube 50 is initially compressed as in FIG. 4 and contains wicking fibers 52 and superabsorbent particles 54. A single liquid soluble seal 56 is located in target area 58. As shown in FIG. 5, after liquid contact, the seal 56 has dissolved, the compressed tube has expanded, and the superabsorbent particles 54 have swollen to further expand the tube 50. This expansion created suction that acted to draw the liquid through the tube to the peripheral area 60. It may also be desirable to have parallel and/or perpendicular channels in liquid communication with the superabsorbent filled tubes to provide additional liquid paths which will not gel block.

Figure 6:
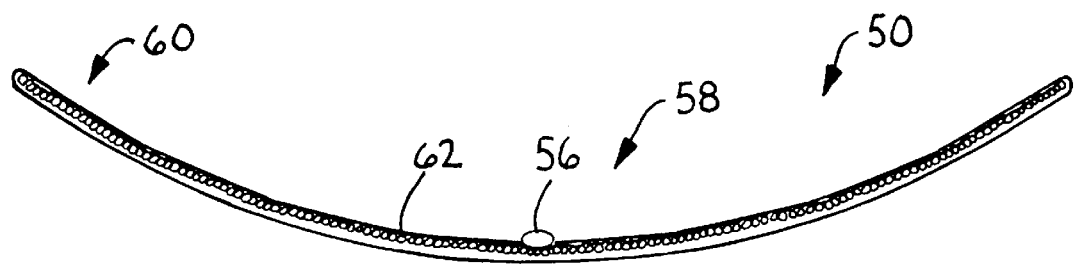
FIG. 6 is a view in cross-section of another liquid movement element in accordance with the present invention prior to liquid contact.
Figure 7:
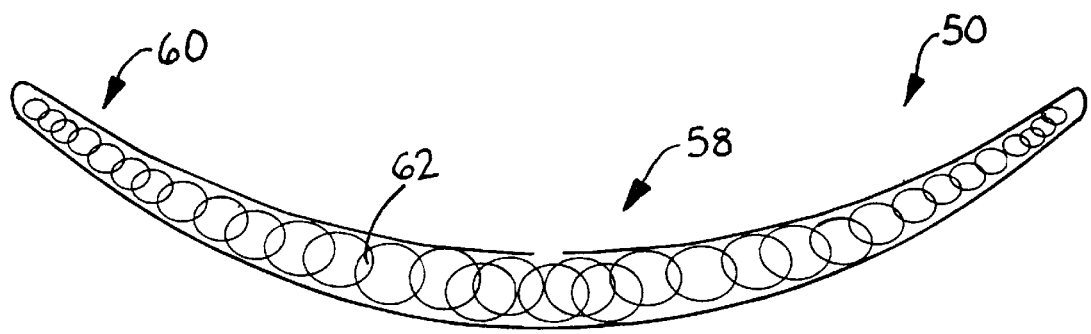
FIG. 7 is a view of the element of FIG. 6 after liquid contact.

FIGS. 6 and 7 are views like that of FIGS. 4 and 5 except that the wicking fibers and superabsorbent particles are replaced by compressed, expandable foam material 62. With a liquid insult and dissolving of seal 56, the material has expanded in FIG. 7 causing the tube 50 to expand and draw liquid through the tube from the target area 58 to the peripheral area 60. The foam could be made up of or contain a superabsorbent material.

Figure 8:
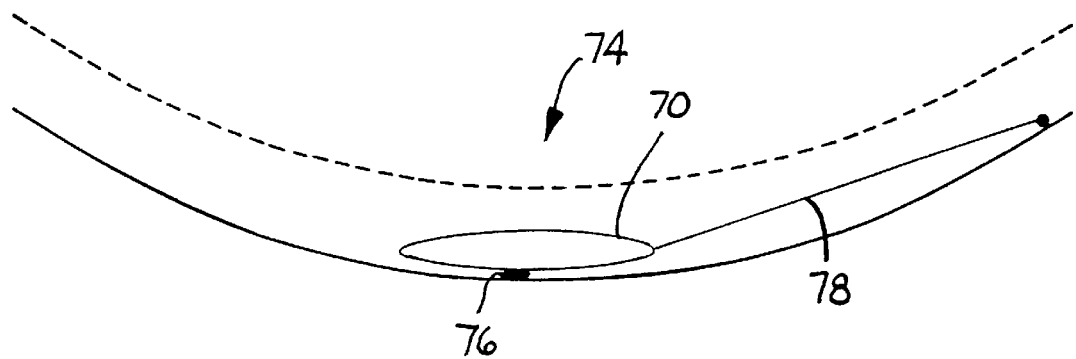
FIG. 8 is a view in cross-section of another liquid movement element in accordance with the present invention prior to liquid contact.
Figure 9:
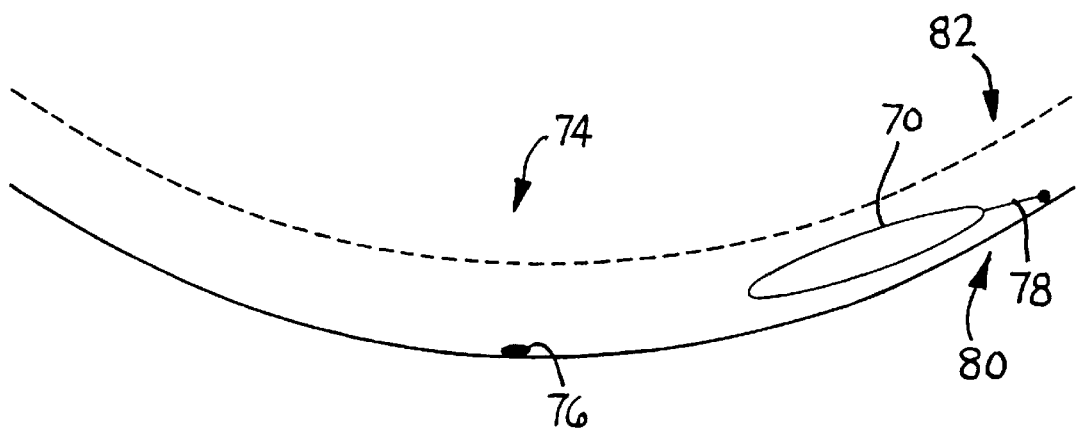
FIG. 9 is a view of the element of FIG. 8 after liquid contact.

FIGS. 8 and 9 illustrate yet another embodiment. In this case, a collection pouch 70 is attached in the target area 74 by liquid soluble attachment seal 76 and connected by retraction band means 78 to position 80 in peripheral area 82. A liquid insult releases pouch 70 containing the liquid to be drawn by retraction means 78 to the peripheral area 82. As will be apparent to those of skill in the art, this arrangement may be facilitated by locating the pouch 70 between layers in the product so that movement can be readily achieved. Also, the point of attachment by the liquid soluble adhesive is desirably away from the first liquid contact point so as to allow the pouch to collect liquid prior to release.

Figure 10:
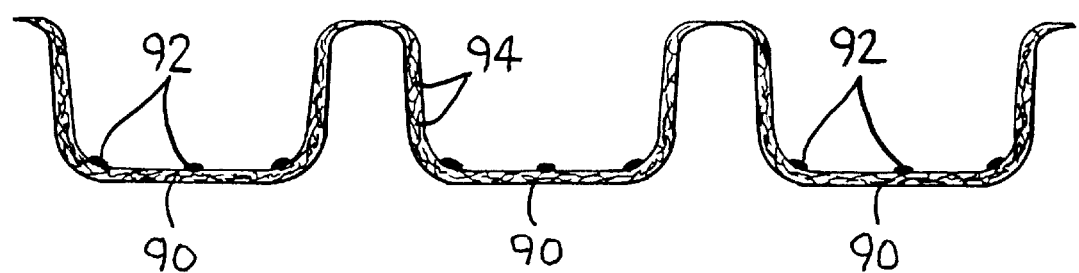
FIG. 10 is a view in cross-section of another liquid movement element in accordance with the present invention prior to liquid contact.
Figure 11:
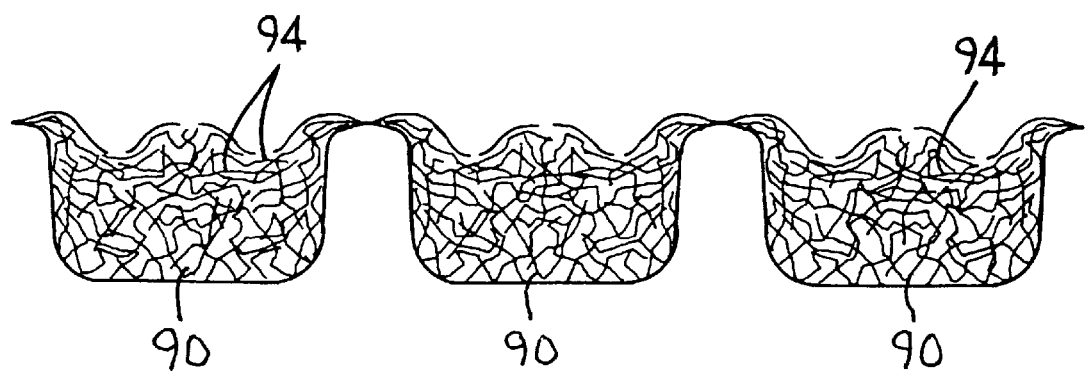
FIG. 11 is a view of the element of FIG. 10 after liquid contact.

FIGS. 10 and 11 illustrate a further embodiment where compressed material including superabsorbent fibers 94 of the type described is formed into channels 90 that have a plurality of liquid soluble seals 92. When contacted with a liquid, the channels 90 expand in a controlled manner to deliver liquid along the channels to the peripheral zones (not shown).

Other embodiments of the invention will be apparent that provide for mass liquid movement by liquid activated mechanical means causing liquid to be drawn from a target zone to a peripheral zone. Also as has been shown, the different embodiments may be used in single or multiple form and, of course, can be combined for even greater effect. The particular application well as cost and ease of manufacture considerations will help determine the best construction in each case.

As will also be appreciated by those skilled in the art, selection of materials for the structures of the invention must be made from those that will achieve the desired results. Examples for specific applications will be given although others will suggest themselves to those of ordinary skill and are intended to be embraced by the description herein and the appended claims.

The liquid soluble seals and attachment means used will depend on the nature of the liquid for which the product is intended. For disposable diaper applications to contain aqueous liquids like urine and runny bowel movement ("BM"), for example, water soluble adhesive compounds based on polyvinyl alcohol can be used. Specific examples include the ELVANOL® brand series of fully hydrolyzed, partially hydrolyzed and copolymers of PVOH available from DuPont as well as TEXTAC® series of water soluble adhesives available from Texas Screen Process Supply Company, Dallas, Tex. It is, of course, not necessary that the seal partially or totally dissolve so long as it releases. Compounds that lose adhesive properties on liquid contact may also be used.

The material used for containment of the liquid in tubes, bags and the like as described for mass transport must, of course not be liquid soluble, at least under conditions of use. The containment structures must also be sufficiently "robust" or have physical properties that maintain the ability to provide mass transport under use conditions. For disposable diaper applications, these containment tubes, bags and the like may be made from inexpensive polymeric materials such as polyolefins, polyesters and the like. For those embodiments requiring stretch of the containment devices, thermoplastic elastomers such as Kraton® brand from Shell Chemical Company of Houston Tex. can be used. KRATON® block copolymers are available in several different formulations, a number of which are identified in U.S. Pat. Nos. 4,663,220 and 5,304,599, hereby incorporated by reference in their entireties. Polymers composed of an A-B-A-B tetrablock copolymer may also be used in the practice of this invention. Such polymers are discussed in U.S. Pat. No. 5,332,613 to Taylor et al. In such polymers, A is a thermoplastic polymer block and B is an isoprene monomer unit hydrogenated to substantially a poly(ethylene-propylene) monomer unit. An example of such a Tetrablock copolymer is a styrene-poly(ethylene-propylene)-styrene-poly(ethylene-propylene) or SEPSEP block copolymer available from the Shell Chemical Company of Houston, Tex. under the trade designation KRATON®.

A particular well suited tube is made from a TYGON® tube having an outside diameter of about 1.3 centimeters, an inside diameter of about 1.9 centimeters, and a length of about 17.8 centimeters. Other suitable materials from which the liquid transfer tubes may be are manufactured are commercially available from Baxter Diagnostics, a business having offices located in McGraw, Ill. under the trade designation S-50-HL. Another suitable tube is available from Advanced Technology Products Co., a business having offices located in Milford Center, Ohio, under the trade designation 532-30-WH and having an inside diameter of from about 0.2 to about 0.7 centimeters.

For suction devices like bulbs and the like that must expand to pull liquid to the peripheral zone, somewhat stronger resilient materials may be used. Examples include thicker versions of the previously mentioned polymers for the tubes as well as other resilient materials capable of maintaining a compressed form and then reacting under changed conditions to expand.

For those embodiments using a compressed expandable foam material, such foams are also known and include, for aqueous liquid applications, regenerated cellulose and other compressible/expandable foams. Suitable materials include expandable foams, compressed cellulose sponges, or the like. Particularly desirable expandable foams include those having open, large cell, reticulated structures. Examples of such expandable foams are available from O-Cell-O, General Mills, Inc., Tonawanda, N.Y., USA, and Industrial Commercial Supply Co., Akron, Ohio, USA. The material may be softened by mechanical means or other suitable techniques so as to be less noticeable until urination occurs. One such means that is effective with compressed cellulose sponge is to run the material through a set of meshed gears with the gap between the gears set so that the material is sufficiently scored to make it pliable.

For those embodiments requiring a swelling material to expand a container to create the suction necessary for mass liquid transport, superabsorbents having this property with respect to aqueous liquids are well-known. These are available in a number of forms including fibers, films, foams, particles, and the like as described previously in detail.

For those embodiments using a retractive force to move a liquid collection device, suitable elastic material in a stretched condition may be employed. Such materials include, without limitation, thermoplastic and rubber elastomers, some of which have been previously described. It is also contemplated to use liquid shrinkable materials such as a stretched elastic film or foam coated with a water soluble polymer. The water soluble polymer dissolves on contact with liquid and the elastomer is allowed to retract. Also as previously described, extended superabsorbent fibers or filaments in an extended condition that contract on liquid contact may be used.

The other components of the devices in accordance with the invention are not critical and may be selected from those conventionally used for the particular product as well as such components as may be developed for the purpose. Liquid pervious liners, for example, often comprise nonwovens such as spunbonded polyolefin webs or perforated films. Absorbents used often contain woodpulp fibers and may contain additives such as superabsorbent in powder or fiber form for increased absorbency. The liquid impervious backing may be made from various films of polyolefins and may contain fillers and/or be combined with a nonwoven layer for cloth-like, breathability, or other desired properties. Again depending on the particular use, elements such as fasteners, waist and leg dams, elastic waist or leg cuffs may be added. For additional details of these and other components that are useful, reference is to U.S. Pat. No. 4,704,116 to Enloe dated Nov. 3, 1987 and U.S. Pat. No. 5,865,825 to Schlinz dated Feb. 2, 1999, the full contents of each of which is incorporated herein by reference.

Example 1

Figure 12:
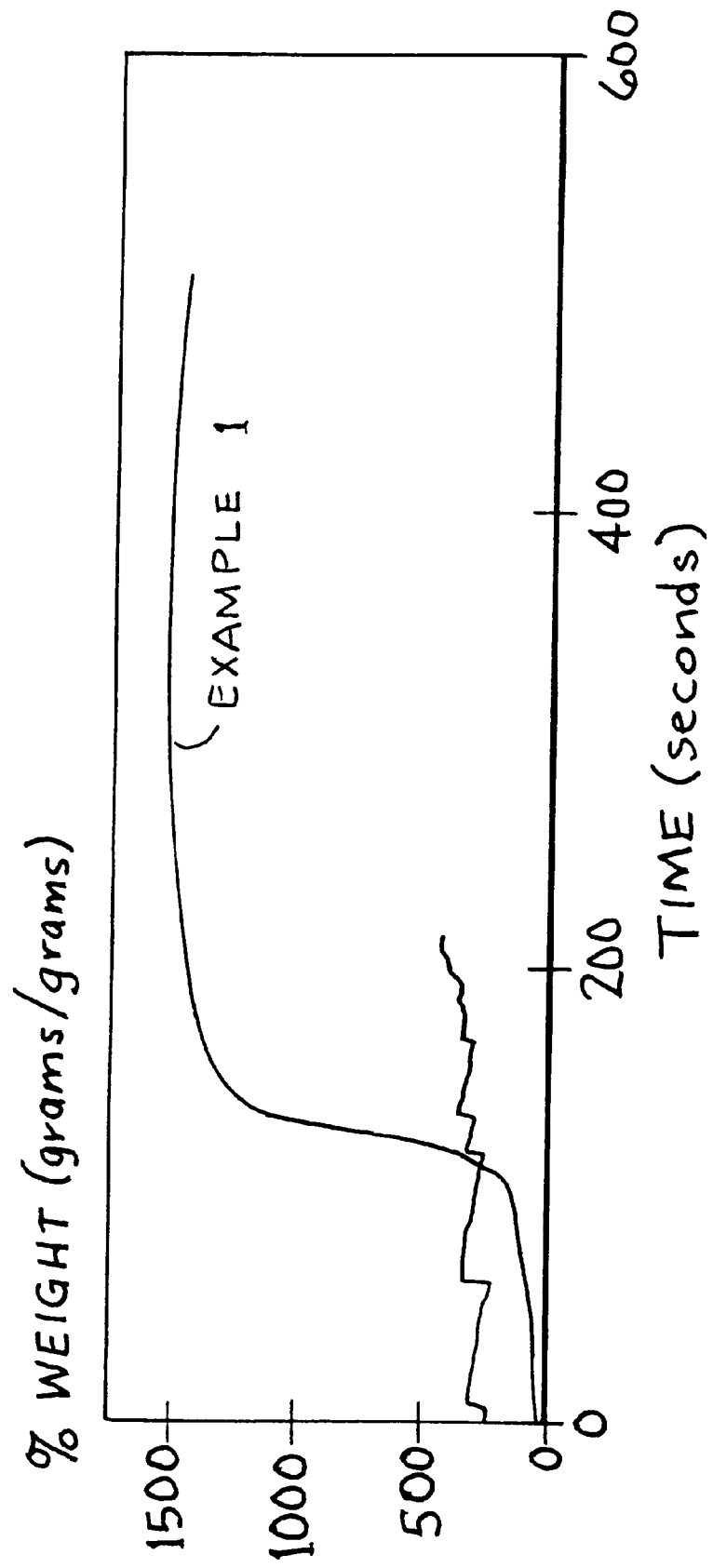
FIG. 12 is a graph of weight change, over time comparing the invention with a standard liquid reception material.

This example demonstrates the ability of vacuum assisted resilient sponge material to draw aqueous liquids by mass transport. A large zip lock plastic bag and an open cell 6 inch by 6 inch auto sponge obtained from Home Depot, Inc. were used. The sponge was placed within the bag and located so as to provide about 5 to 6 inches of space at each end within the bag. The bag and contents were compressed in a hydraulic press until virtually all air was removed and the bag sealed. The sponge partially expanded when the bag was removed from the press creating a partial vacuum inside the bag. A hook was attached to the bottom weighing unit of an electronic balance. The sealed bag was attached to the balance hook with the sealed end immersed in about one to two inches of water. Holes were cut in the sealed end of the bag, and the weight change of the bag over a ten minute period recorded as in FIG. 12 which compares the same sponge material without the vacuum assist.

Example 2

This example demonstrates the use of a tube as a mass transport means in accordance with the invention. A one foot length of plastic tubing (Tygon® B-44-3, ⅜ inch diameter from Norton) was sealed at one end using marine adhesive (Goop® brand). Using a hydraulic press the tube was pressed to essentially force all of the air was evacuated from the tube, and the opposite end sealed using a channel lock vise grip leaving a three inch portion of unevacuated tubing past the seal. Liquid gelatin (Knox® brand or equivalent) was placed into the unevacuated portion, and the tubing was placed in a standard refrigerator to allow the gelatin to solidify. The test used in Example 1 was repeated after the gelatin had solidified except that weight determinations were not made. It was observed that the gelatin acted to regulate the mass liquid transport, and it was noted that there was no discernible change over the first thirty seconds. Then the tube took on water in a matter of a few seconds and, after about thirty seconds, had reassumed its circular cross-section. No change took place over an additional three minutes, but, upon removal, thereafter, the gelatin retained the water within the tube. Thus the gelatin with the vacuum assist extracted the water into the tube then acted as a plug to retain it.

The above description of the best mode and other examples is not exhaustive of embodiments of the invention, and others will be apparent to those of ordinary skill. The appended claims are intended to describe all such embodiments as well as equivalents as may be embraced by the claims.

We claim:

1. A liquid reception device comprising:
   a) a liquid-receiving layer having a target zone;
   (b) a peripheral zone located within or outside said liquid receiving layer;
   (c) mechanical liquid transport means located partially within said target zone and adapted for liquid communication with said peripheral zone and comprising:
      (i) at least one tube having at least one sealed opening within said target zone;
      (ii) suction means for drawing said liquid through said at least one tube from said target zone to said peripheral zone; and
      (iii) opening means for opening said at least one sealed opening activated by contact with said liquid thereby causing said suction means to draw said liquid from said target zone to said peripheral zone.

2. The liquid reception device of claim 1 wherein said suction means comprises a component that expands on contact with said liquid.

3. The liquid reception device of claim 2 wherein said component that expands is selected from the group consisting of roams and superabsorbents.

4. The liquid reception device of claim 2 as a component of a disposable diaper.

5. The liquid reception device of claim 2 as a component of an incontinent product.

6. The liquid reception device of claim 2 as a component of a soaker pad.

7. The liquid reception device of claim 2 as a component of a personal care product.

8. The liquid reception device of claim 2 wherein said mechanical transport means comprises a gelatin liquid retention material.

9. A liquid reception device comprising:
   (a) a liquid receiving layer having a target zone;
   (b) a peripheral zone located within or outside said liquid receiving layer; and
   (c) mechanical liquid transport means located partially within said target zone and adapted for liquid communication with said peripheral zone, said mechanical transport means comprising:
      (i) at least one tube having at least one sealed opening within said target zone;
      (ii) suction means comprising a component that expands on contact with said liquid for drawing said liquid through said at least one tube from said target zone to said peripheral zone; and
      (iii) opening means for opening said at least one said sealed opening activated by contact with said liquid thereby causing said suction means to draw said liquid from said target zone to said peripheral zone.

* * * * *